United States Patent [19]
Lee et al.

[11] Patent Number: 5,807,758
[45] Date of Patent: Sep. 15, 1998

[54] CHEMICAL AND BIOLOGICAL SENSOR USING AN ULTRA-SENSITIVE FORCE TRANSDUCER

[76] Inventors: Gil U. Lee, 913 Washington St., Alexandria, Va. 22314; David A. Kidwell, 6125 Florence La., Alexandria, Va. 22310; Richard J. Colton, 7401 Calico Ct., Springfield, Va. 22153

[21] Appl. No.: 505,547

[22] Filed: Jul. 21, 1995

[51] Int. Cl.$^6$ .............................. C12Q 1/70; C12Q 1/68; C01N 33/573; G01N 33/573; G01N 27/00
[52] U.S. Cl. ................... 436/526; 435/5; 435/6; 435/7.7; D22/82.01; 250/306; 204/290 R
[58] Field of Search .................... 435/6, 5, 7.4; 436/526; 204/290 R; 250/306; 422/82.01

[56] References Cited

U.S. PATENT DOCUMENTS

| | | | |
|---|---|---|---|
| 4,222,744 | 9/1980 | McConnell | 23/230 |
| 5,372,930 | 12/1994 | Colton | 435/6 |
| 5,445,970 | 8/1995 | Rohr | 436/526 |
| 5,445,971 | 8/1995 | Rohr | 436/526 |

Primary Examiner—Kenneth R. Horlick
Assistant Examiner—Joyce Tung
Attorney, Agent, or Firm—Thomas E. McDonnell; John J. Karasek

[57] ABSTRACT

The present invention is a method and apparatus for detecting a target species. The target molecule may be in liquid phase (in solution) or (for some embodiments of the invention) in vapor phase. A sensor according to the present invention monitors whether a target species has selectively bound to groups on the cantilever surface by monitoring the displacement of the cantilever, and hence the force acting on the cantilever. This force acting on the cantilever arises from the force acting on a structure that moves in electric or magnetic field, and that may be selectively bound to the cantilever. In the case of target species having a sufficiently large net electric charge or dipole moment, the target species itself may serve as the structure that moves in an electric field. More typically however, separate modified structures, such as modified magnetic beads or modified beads having a net charge or a dipole moment, will, when selectively bound to the cantilever, exert a force on the cantilever that relates to the presence of the target species.

32 Claims, 6 Drawing Sheets

CHEMICAL AND BIOLOGICAL SENSOR USING AN ULTRA-SENSITIVE FORCE TRANSDUCER

BACKGROUND OF THE INVENTION

1. Field of the Invention

The present invention relates generally to assays and more specifically to binding assays, such as DNA/RNA or antibody/hapten interactions, taking advantage of labels that respond to an electric or magnetic field.

2. Description of the Related Art

Binding assays, for example, immunoassays and receptor based assays, are widely used in the medical community as diagnostic tests for a wide range of target molecules. There are several binding assays that have been produced and are currently on the market since the principle was developed by R. S. Yalow and S. A. Berson.

As used herein, a target molecule encompasses both molecules whose presence, absence, or concentration one is interested in determining, as well as capture molecules that may be released in the presence of a molecule whose presence, absence, or concentration one is interested in determining. In the latter case the assay is an indirect assay, rather than a direct assay. For example, a column may contain antibodies bound to a bead labelled with two antigens (e.g., cocaine and biotin). The binding of the bead to the column is through interaction with the cocaine moiety on the bead and the antibody on the column. A solution of cocaine flowing through the column may displace some of the bound beads, and carry them to the sensor which, in this case, would contain streptavidin, avidin, or an antibody that binds the second label (here, biotin). The sensor section is what is used to detect the bead, and indirectly the cocaine in the introduced solution, because the bead would only be released in the presence of cocaine.

All immunoassays exploit the binding capabilities of antibodies. However other molecules (e.g., chelators, strands of polynucleic acids, receptors including cellular receptors) that are capable of recognizing and selectively binding other molecules may be employed to detect a wide range of species, such as polynucleic acids (DNA or RNA) or strands of polynucleic acids, enzymes and other proteins, polymers, metal ions, and certain low molecular weight organic species including a number or illegal drugs. Antibodies are protein molecules which are frequently considered fighters of infections. They fight infections by binding to the infectious material in a specific manner, forming a complex. This is a signal to the organism to reject that complex. However, antibodies may also be produced to bind to an individual compound, as a key fits a lock. To be useful in an assay, this recognition event must generate a signal that is macroscopically observable. The method employed to generate such a signal is what distinguishes the various types of immunoassays. In the initial embodiment of an immunoassay, radioactivity was employed. RIA is quite sensitive and widely used, but the expense and restrictions for handling radioactive material, plus the labor involved in performing the assay, makes alternative immunoassays desirable.

Surface acoustic wave (SAW) detectors use substrates with coatings that selectively bind to target molecules of interest. When the target species binds to the coating, the additional mass of the coating will change the resonant frequency of a substrate surface acoustic wave. SAW detection is only suitable for vapor phase analysis: it has not been made to work in solution. See U.S. patent application Ser. No. 07/970,750.

Cantilevers micromachined from silicon or silicon nitride with sub-millimeter lengths and widths and thicknesses less than 10 $\mu$m have both small spring constants and high resonance frequencies. See Albrecht, T. R., Akamine, S., Carver, T. E., Quate, C. F. (1990) J. Vac. Sci. Technol. A 8(4) 3386–3396. For example, the spring constant of a 500×5×1 $\mu$m silicon nitride cantilever is $6 \times 10^{-4}$ N/m and its resonance frequency is 3.3 kHz. If the deflection of the cantilever is monitored with a displacement sensor, a force detector is produced. Force detectors using micromachined cantilevers and interferometers have achieved sensitivities of $10^{-15}$ N/$\sqrt{Hz}$ and have been used to measure the forces between individual ligand-receptor interactions. See Zuger, O., Rugar, D. (1993) Appl. Phys. Lett. 63(18) 2496 et seq.; Lee, G. U., Kidwell, D. A., Colton, R. J. (1994) Langmuir 10 (2) 354–357.

The microfabricated cantilever was originally developed for atomic force microscopy but has recently been utilized in biological and chemical sensing. The proximal probe biological and chemical sensor measures the forces arising from molecular recognition events between a chemically modified probe (attached to the microfabricated cantilever) and a chemically modified surface. See U.S. Pat. No. 5,372,930.

Two other chemical sensors based on microfabricated cantilevers have been described in the literature recently. One sensor utilized the thermally induced stress produced by reactions catalyzed on the metallic coating of the cantilever. See Gimzewski, J. K., Gerber, C., Meyer, E., Schlittler, R. R. (1994) Phys. Chem. Two limitations of this sensor are that it operates most effectively in vacuum (requiring substantial instrumentation and making it unsuitable for most biological interactions that are desired) and it is limited in specificity by the reactivity of the metal coating.

Another sensor uses the change in the resonance frequency of the cantilever due to the mass of the chemical species, in a manner analogous to the change observed in a SAW frequency. See Thundat et al., Applied Physics Lett. 64 2894–96 (1994). Mercury was non-specifically detected in the demonstration of the sensor, although the authors note that chemically active surfaces may be used for the specific identification of analytes. Although the microfabricated cantilever is ultra-sensitive to mass loading, the sensor sensitivity is limited by the fact that operating in fluids diminishes the effect of mass of the analyte due to buoyancy and damping.

Most or all binding assays have the following features in common: they exploit some labelling phenomenon where this label may be detected with very high sensitivity. RIA, for example, uses the ease of detection and lack of background noise for radioactivity. See D. S. Skelley et al., "Radioimmunoassay, Clinical Chem. 19 (2) 146–186 (1973). Chemiluminescence exploits, in the use of its labelling scheme, the sensitive detection of photons of light as well as the small number of molecules that produce chemiluminescence. Fluorescence assays, although less sensitive than chemiluminescence or RIA due to background interferences, takes advantage of fluorescent labels that can be detected with excitation and emission wavelength selectivity. See R. F. Schall et al., "Alternatives to Radioimmunoassay: Labels and Methods", Clinical Chem. 27 (7) 1157–64 (1981).

An improved binding assay sensor would share these features, and additionally would not require a separation of the unbound, labelled species from the bound, labelled species as a step taken by the user.

SUMMARY OF THE INVENTION

Accordingly, it is an object of this invention to selectively detect a wide range of target species, in either vapor or liquid phase, with a high degree of sensitivity.

It is a further object of this invention to detect target species using a transduction mechanism that is independent of the mass of the species, and does not require a separation step.

These and additional objects of the invention are accomplished by the structures and processes hereinafter described.

The present invention is a method and apparatus for detecting a target species. The target molecule may be in liquid phase (in solution) or (for some embodiments of the invention) in vapor phase. A sensor according to the present invention monitors whether a target species has selectively bound to groups on the cantilever surface by monitoring the displacement of the cantilever, and hence the force acting on the cantilever. This force acting on the cantilever arises from the force acting on a structure or structures that move in electric or magnetic field (defined herein as electrically or magnetically active structures), and that may be selectively bound to the cantilever. In the case of target species having a sufficiently large net electric charge or dipole moment, the target species itself may serve as the structure that moves in an electric field. More typically however, separate modified structures, such as modified magnetic beads or modified beads having a net charge or a dipole moment, will, when selectively bound to the cantilever, exert a force on the cantilever that relates to the presence of the target species. In other words, an electrically or magnetically active structure may be a molecule, colloidal particle, bead, etc., that will move in an electric or magnetic field.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DETAILED DESCRIPTION OF THE PREFERRED EMBODIMENTS

Magnetic Field Embodiments

Paramagnetic materials have a net magnetization $\mu$ only in the presence of an applied external field B. Nonporous paramagnetic beads (usually made from an impregnated polymer) are used for magnetic separation in molecular biology because of their relatively low density and lack of residual magnetism. They may also have surface functional groups (such as amine or carboxyl) that may be used to covalently immobilize receptors (e.g., streptavidin, antibodies, or DNA). See Technical Handbook of the Dynal Co, 5 Delaware Dr., Lake Success, N.Y. 11042; Lund, V., Schmid, R., Richwood, D., Hornes, E. (1988) 16 (22) 10861–10880; Wang, N., Butler, J. P., Ingber, D. E. (1993) Science 260, 1124–1127. Magnetic beads can be used for separation of analytes in complex mixtures by immobilization of the analyte on the bead followed by separation of the beads in a magnetic field. Several patents and patent applications have described the use of magnetic beads for detection applications.

The force acting on a small paramagnetic specimen in a nonuniform magnetic field is given by $$F = \mu \frac{\partial B}{\partial x}$$

where $\mu$ ($=\chi B$) is the magnetization (i.e., magnetic dipole moment) of the specimen, and $$\frac{\partial B}{\partial x}$$

is the magnetic field gradient.

Thus, a preferred embodiment of the invention includes a cantilever having attached chemical groups, disposed in solution and in a nonuniform magnetic field, and one or more paramagnetic beads, disposed in the solution, where the beads have been chemically modified to have a selective binding response relative to the attached chemical groups on the cantilever in the absence of the target molecule, and a different selective binding response relative to the attached chemical groups on the cantilever in the presence of the target molecule.

Figure 1:
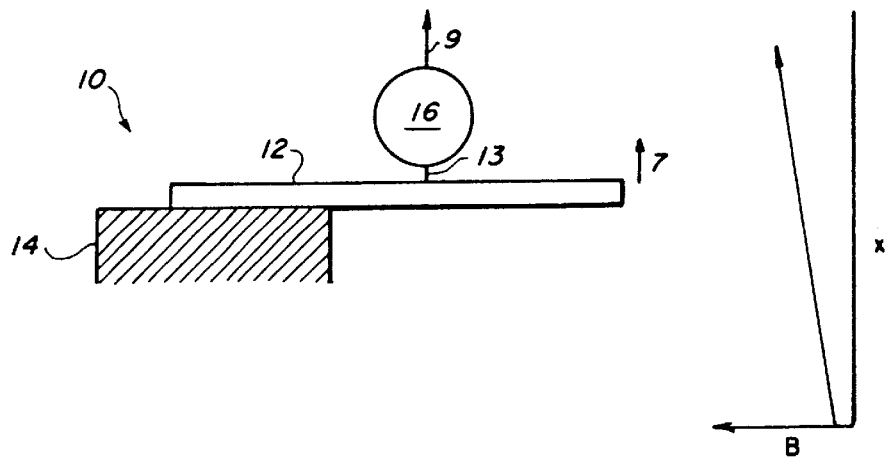
FIG. 1 shows the interaction of a paramagnetic bead label in a nonuniform magnetic field with a cantilever in a method and apparatus of the invention.

As shown in FIG. 1, in this preferred embodiment of the invention 10, when a paramagnetic bead 16 is bound to a cantilever 12 through a linkage 13, in a nonuniform magnetic field (as depicted by the graph), the magnetic force acting on this bead (shown by arrow 9) will cause the cantilever to move relative to its base 14, as indicated by arrow 7. However, when no paramagnetic bead is bound to the cantilever, then there will be no force causing the cantilever to move. Moreover, the force on the cantilever 12, and hence its deflection, will scale roughly linearly with the number of paramagnetic beads 16 bound to the cantilever 12.

Paramagnetic beads are desired for this embodiment of the invention, because the beads will have a magnetization only when an external field is applied. Thus, the beads will not tend to clump together, which would potentially interfere with their interaction with the cantilever and/or a target species. However, ferromagnetic beads may be substituted, especially if certain precautions are taken.

Ferromagnetic materials have a net magnetization $\mu$ after being magnetized in an applied magnetic field. This magnetization is permanent until a coercive field is applied, or until the material is raised above its Curie temperature. Nonporous ferromagnetic beads are also available. Like paramagnetic beads, they may also have surface functional groups that may be used to covalently immobilize receptors. See Wang, N., Butler, J. P., Ingber, D. E. (1993) Science 260, 1124–1127.

If ferromagnetic beads are used, however, they generally should either (1) be kept above their curie temperature until, in situ, one is ready to perform an analysis, or (2) not be magnetized in a magnetizing field until, in situ, one is ready to perform an analysis.

A method according to the present invention for detecting the presence of a target substance in a sample suspected of including the target substance, where the target substance selectively binds to species having a binding site for the target substance, includes the steps of placing the sample in a solution in a magnetic field and in contact with a cantilever modified with chemical groups; placing in the solution one or more paramagnetic beads, where these beads have been modified with chemical groups having a selective binding response relative to the attached chemical groups on the cantilever in the absence of the target substance, and a different selective binding response relative to the attached chemical groups on the cantilever in the presence of the target substance; and monitoring the cantilever for displacement or force.

Electric Field Embodiments

Another sensor according to the invention includes a cantilever having attached chemical groups, disposed in an electric field, where the attached chemical groups on the cantilever exhibit a selective binding response in the absence of the target molecule, and a different selective binding response in the presence of the target molecule. Optionally, this sensor includes beads having a net electrical charge (typically due to ionization of functionalities—such as amine groups, carboxylic acids, or sulfonic acids—contained either in or on the surface of the bead) or a dipole moment, where these beads have been chemically modified to have a selective binding response relative to the attached chemical groups on the cantilever in the absence of the target molecule, and a different selective binding response relative to the attached chemical groups on the cantilever in the presence of the target molecule. Alternatively, the target species itself has either a net magnetic charge or a dipole moment.

The force acting on a small specimen having charge q in an electric field E is given by $$F=qE.$$

Figure 2:
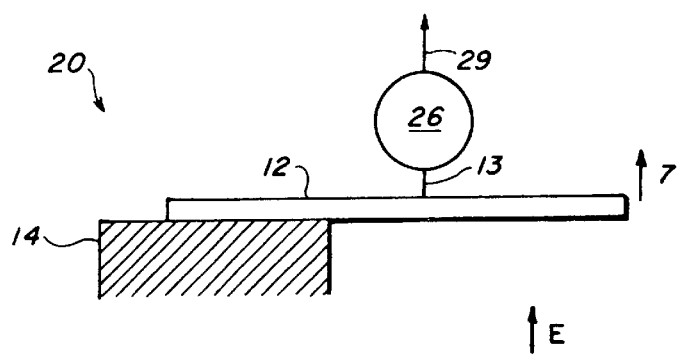
FIG. 2 shows the interaction of a charged bead label in an electric field with a cantilever in a method and apparatus of the invention.

Small beads which may be charged and chemically modified are readily available. Thus, as shown in FIG. 2, in this preferred embodiment of the invention 20, when a charged bead 26 is bound to a cantilever 12 through a linkage 13, in an electric field, the electric force acting on this bead (shown by arrow 29) will cause the cantilever 12 to move relative to its base 14, as indicated by arrow 7. However, when no charged bead is bound to the cantilever, then there will be no force causing the cantilever to move. Moreover, the force on the cantilever 12, and hence its deflection, will scale roughly linearly with the number of charged beads 26 bound to the cantilever 12.

Figure 3:
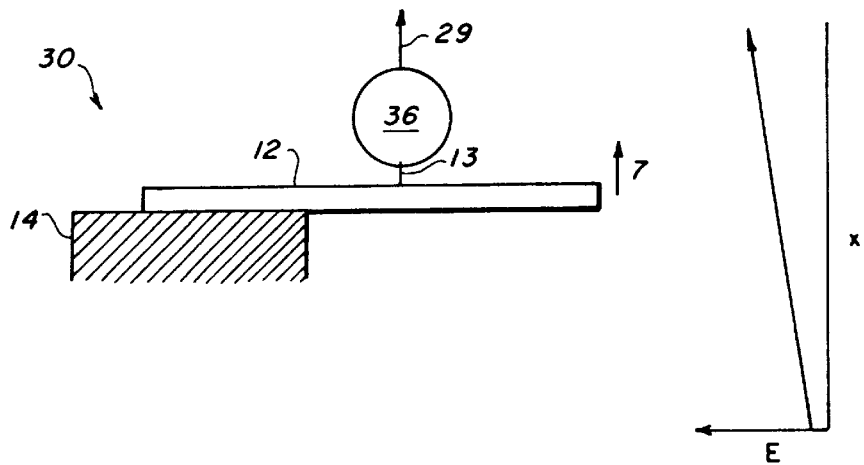
FIG. 3 shows the interaction of a dipolar bead label in a nonuniform electric field with a cantilever in a method and apparatus of the invention.

Alternatively, electrically dipolar beads may be used in a non-uniform electric field, although the forces arising from the movement of dipoles in non-uniform electric fields usually will be smaller than forces arising from the movement of electrostatically charged bodies in electric fields. Thus, as shown in FIG. 3, in this embodiment of the invention 30, when an electrically dipolar bead 36 is bound to a cantilever 12 through a linkage 13, in a nonuniform electric field, the electric force acting on this bead (shown by arrow 29) will cause the cantilever 12 to move relative to its base 14, as indicated by arrow 7. However, when no electrically dipolar bead is bound to the cantilever, then there will be no force causing the cantilever to move. Moreover, the force on the cantilever 12, and hence its deflection, will scale roughly linearly with the number of electrically dipolar beads 36 bound to the cantilever 12.

A method according to the present invention for detecting the presence of a target substance in a sample suspected of including the target substance, where the target substance selectively binds to species having a binding site for the target substance, includes the steps of: placing the sample in a solution in an electric field and in contact with a cantilever modified with chemical groups; placing in the solution one or more beads having a net charge or a dipole moment, where these beads have been modified with chemical groups having a selective binding response relative to the attached chemical groups on the cantilever in the absence of the target substance, and a different selective binding response relative to the attached chemical groups on the cantilever in the presence of the target substance; and monitoring the cantilever for displacement or force.

In cases where the target species is itself a charged species or a species with a significant dipole moment, the need for a separate charged or dipolar structure (usually a bead, as described above) may be obviated. For instance, polynucleic acids and heparin have large charges. Many proteins have smaller, but still significant charges. Also, many species which do not have a significant charge in one pH range may have a significant charge in a different pH range. Likewise, many species which do not have an intrinsic dipole moment may have a dipole moment induced by the presence of an electric field.

Figure 4:
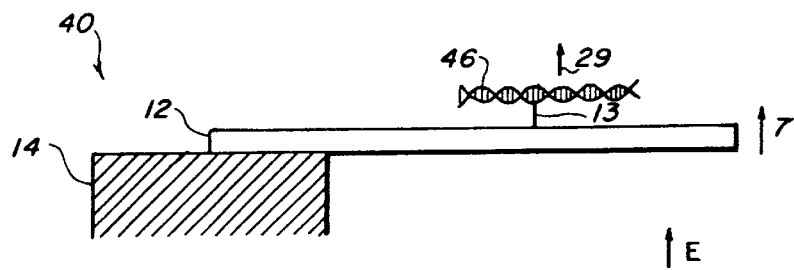
FIG. 4 shows the interaction of a charged target species such as DNA in an electric field with a cantilever in a method and apparatus of the invention.

Thus, as shown in FIG. 4, in this preferred embodiment of the invention 40, when a charged or dipolar target species 46 (shown here as a DNA strand) is bound to a cantilever 12 through a linkage 13, in an electric field, the electric force acting on this species (shown by arrow 29) will cause the cantilever 12 to move relative to its base 14, as indicated by arrow 7. However, when no species is bound to the cantilever, then there will be no force causing the cantilever to move. Moreover, the force on the cantilever 12, and hence its deflection, will scale roughly linearly with the number of species 46 bound to the cantilever 12.

For a target species that is itself a charged species or a species with a significant dipole moment, and that is volatile in some temperature range, this species may be analyzed in vapor phase according to the present invention, because the need for charged or dipolar beads has been obviated.

A method according to the present invention for detecting the presence of a target substance in a sample suspected of including the target substance, where the target substance selectively binds to species having a binding site for the target substance, includes the steps of: placing the sample in a solution in an electric field and in contact with a cantilever modified with chemical groups; placing in the solution one or more beads having a net charge or a dipole moment, where these beads have been modified with chemical groups having a selective binding response relative to the attached chemical groups on the cantilever in the absence of the target substance, and a different selective binding response relative to the attached chemical groups on the cantilever in the presence of the target substance; and monitoring the cantilever for displacement or force.

The present invention may be configured to detect target species by way of a sandwich assay, a displacement assay, or a competitive assay. Each of these will be described in more detail below, in the context of a detector and a detection scheme using a non-uniform magnetic field. It should be recognized, however, that target species may be detected according to the present invention in a sandwich assay, a displacement assay, or a competitive assay while working in either a magnetic field or an electric field, as described above.

Each of these embodiments has a modified cantilever, an electric or magnetic field, and magnetically or electrically active species or structures that selectively bind to the modified cantilever in a manner that depends on the concentration of the target species and move in a suitable applied electric or magnetic field.

Sandwich Assay Embodiments

Figure 5:
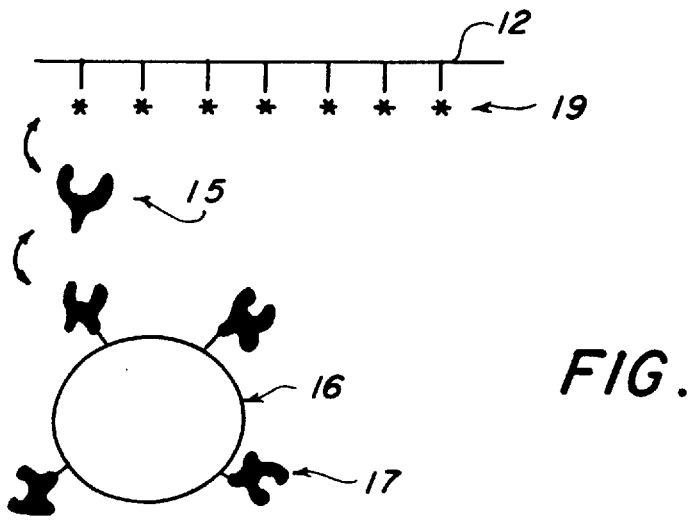
FIG. 5 shows the selective interactions in a sandwich assay embodiment of the invention.

As shown in FIG. 5, some target species 15 (such as immune complexes and targets with a plurality of epitopes) will selectively bind to at least two binding species 17,19, and thus may be sandwiched by these species. Thus, in a sandwich assay embodiment of the invention, the cantilever 12 is modified with a species 19 that will selectively bind to the target 15, and the magnetic bead 16 is modified with a species 17 that will selectively bind to the target 15. In the presence of the target species 15, the modified bead 16 will be bound to the modified cantilever 12, through the specific binding interactions between the target 15 and the cantilever species 19, and the target and the bead species 17. When so bound to the cantilever, the bead will move in the applied magnetic field and thereby deflect the cantilever, thus signaling the presence of the target 15.

Although FIG. 5 shows the receptor sites on the bead and the ligand sites on the cantilever, these may be interchanged, as skilled practitioners will recognize.

In this embodiment of the invention, the species 15 may be prebound to the species 17 on the bead 16, prebound to species 19 on the cantilever 12, or the species 15 and the bead 16 may be introduced together.

Displacement Assay Embodiments

Figure 6:
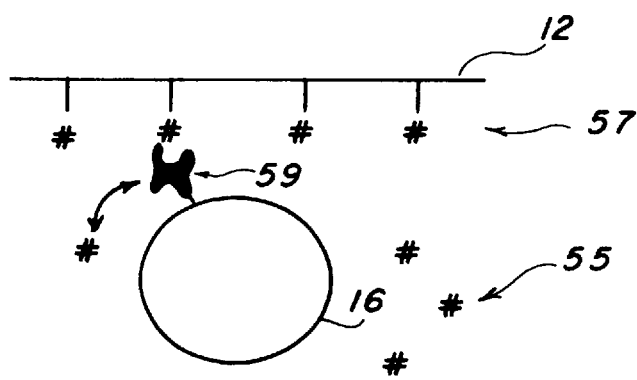
FIG. 6 shows the selective interactions in a displacement assay embodiment of the invention.

As shown in FIG. 6, some target species 55 will displace a species 59 that selectively binds to another species 57. Thus, in a displacement assay embodiment of the invention, the cantilever 12 is modified with a species 57 that will selectively bind to the species 59 modifying the magnetic bead 16. Prior to the introduction of a sample suspected of containing the target 55, the species on the bead is selectively bound to the species on the cantilever. The force from the field acting on the bead causes the displacement of the cantilever, indicating the absence of the target. In the presence of the target species 55, the bead will be displaced. The force (which may be from the interaction of the bead with the electric or magnetic field) on the cantilever will be reduced, and accordingly the displacement of the cantilever will be reduced, thus signalling the presence of the target species.

Although FIG. 6 shows the receptor sites on the bead and the ligand sites on the cantilever, these may be interchanged, as skilled practitioners will recognize.

Competition Assay Embodiments

Figure 7:
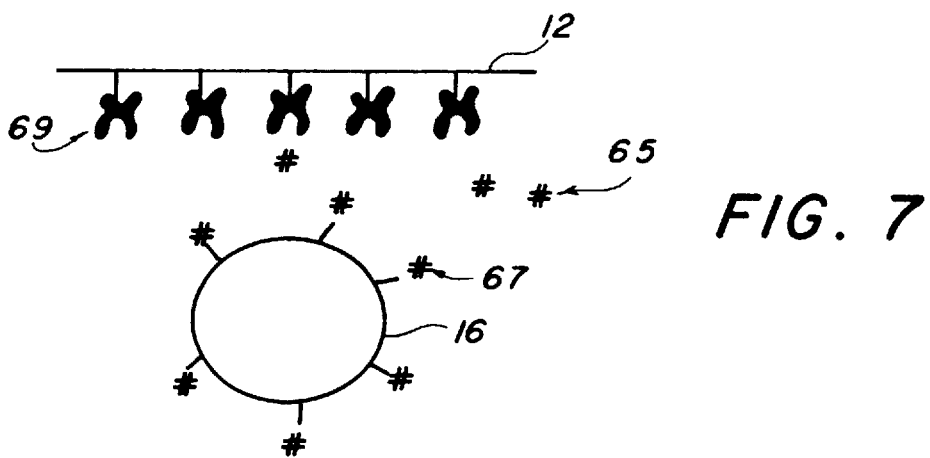
FIG. 7 shows the selective interactions in a competitive assay embodiment of the invention.

As shown in FIG. 7, some target species 65 will compete with species 67 on a magnetic bead 16 to selectively bind to species 69 on a cantilever 12. Thus, in a competitive assay embodiment of the invention, the cantilever 12 is modified with species 69 that will selectively bind to the target species 65 and species 67 on the magnetic bead. In the presence of the target species 65, the target species 65 will compete with the species 67 on the magnetic bead 16 for binding sites on the species 69 bound to the cantilever 12. To the extent that the target species 65 successfully compete for these binding sites, the bead 16 will not bind to the cantilever 12, and the cantilever will not be deflected due to the force acting on the cantilever from the applied field, thereby indicating the presence of the target species 65.

Although FIG. 7 shows the ligand sites on the bead and the receptor sites on the cantilever, these may be interchanged, as skilled practitioners will recognize.

In this embodiment of the invention, one may prebind the species 65 to the species 69 on the cantilever 12 before exposure to the species 67 on the bead 16, or they may be introduced together. This prebinding may occur in the vapor phase, or in solution.

Deflection Monitoring

A large number of methods may be employed to monitor the deflection of the cantilever, including optical lever, fiber optic interferometer, interferometer, tunnelling, capacitance, single diode, and piezoresistive cantilever detection schemes. Each of these detection schemes has advantages and disadvantages that will be recognized by skilled practitioners in the art. Piezoresistive detection, although potentially less sensitive than other detection schemes, should provide robust operation in a wide range of field use environments.

Noise Reducing Embodiments

Sources of noise for the present invention may include vibrations (which would provide an accelerating force on the cantilevers, creating spurious signals), non-specific binding of the electrically or magnetically active species (i.e., the beads or the charged or dipolar target species) such as hydrogen bonding or non-specific adsorption, voltage source noise, and undesired electromagnetic interactions.

Figure 8:
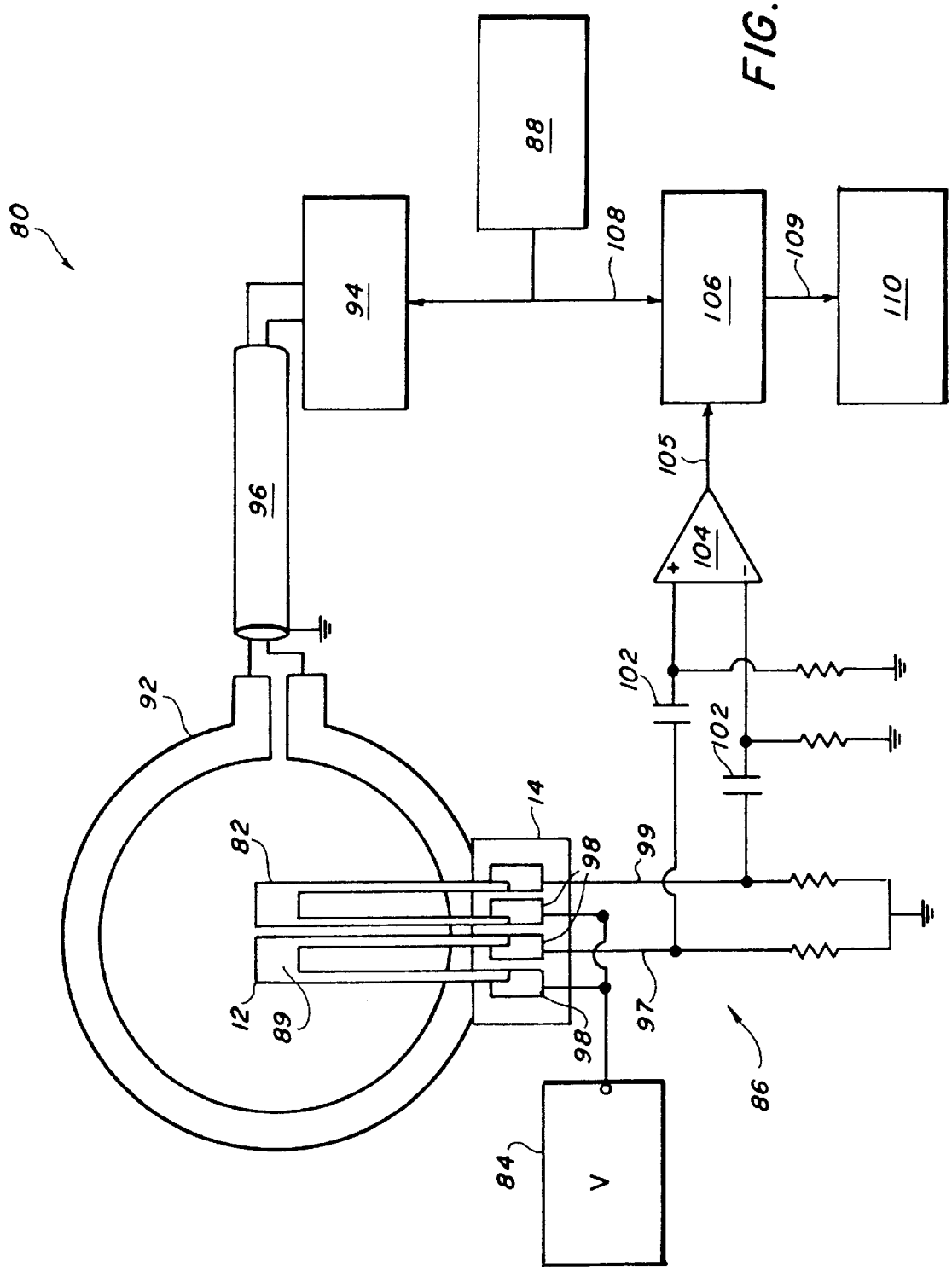
FIG. 8 shows a schematic of a preferred apparatus according to the invention.

As shown in FIG. 8, a preferred embodiment 80 of the invention preferably includes a reference cantilever 82 in proximity to the modified cantilever 12. With the two cantilevers 12,82 preferably in proximity, they should be exposed to the same vibrations and undesired electromagnetic interactions. With the two cantilevers 12,82 preferably connected in parallel to a common voltage source 84, they should be exposed to the same voltage source noise. With the two cantilevers 12,82 being preferably identical (except for the modifiers 89 for specific binding on the modified cantilever 82), they should undergo similar non-specific binding. By preferably connecting these two cantilevers 12,82 in a wheatstone bridge 86, these sources of noise may be mitigated or eliminated.

Figure 9:
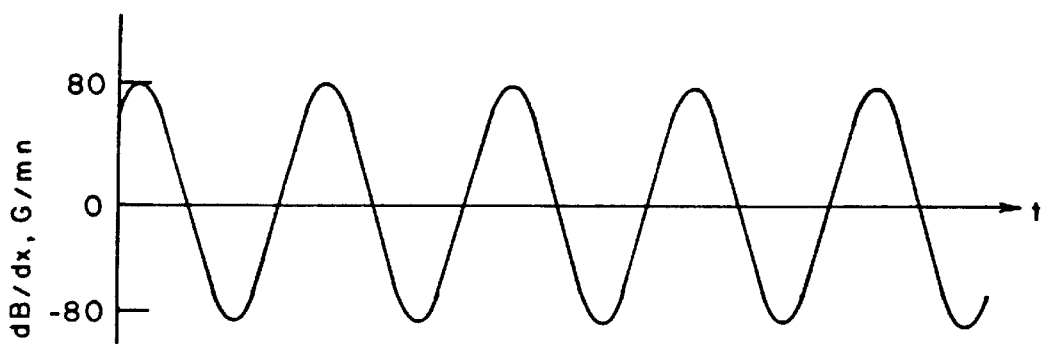
FIG. 9 shows a preferred varying magnetic field gradient used in a preferred embodiment of the invention.

As further shown by FIG. 8, lock-in techniques may be used to further reduce or eliminate noise by narrowing the bandwidth of the system to a regime where most noise has been eliminated. As shown by FIG. 8, a signal from a sine wave generator 88 is directed to two parallel Helmholtz coils 92 (only one of which is shown, for clarity of illustration) on opposing sides of the cantilevers 12,82, through a current buffer 94 and a twinaxial cable 96 for shielding. Typically, the Helmholtz coils are connected in series. Preferably, the field generated between the Helmholtz coils whose gradient $$\frac{\partial B}{\partial x}$$

varies with time, at some selected frequency, as shown in FIG. 9.

Referring back to FIG. 8, the preferred piezoresistive elements 98 are coupled to the cantilevers 12,82 so that the piezoresistive elements 98 are strained as a function of the cantilever 12,82 deflections. The outputs 97,99 of the piezoresistive elements 98 preferably are directed through a pair of high-pass filters 102 (one for each output), and directed into the inputs of a differential amplifier 104. The output 105 of the differential amplifier 104 is then preferably directed into a lock-in amplifier 106, with a reference input 108 from the sine wave generator 88. The output 109 of the lock-in amplifier 106 is then preferably directed into a computer 110 for further signal processing.

Embodiments Employing Various Field-Producing Methods

In embodiments of the invention where paramagnetic beads are employed, it will be necessary to provide means for (1) producing a field for magnetizing the paramagnetic beads, so that they have a electric moment $\mu$, and (2) producing a magnetic field gradient, either oscillating (as described above) or constant, so that there is a force acting on the magnetized beads. Skilled practitioners will recognized that these features may be provided in a single system providing both the magnetizing field and the field gradient, or in separate systems, where one system provides the field and the other system provides the field gradient.

In the embodiment described above, and illustrated in FIG. 8, a pair of opposing Helmholtz coils are employed to produce the field gradient for providing the force on the magnetic beads associated with both of the cantilevers. Alternatively, smaller pairs of opposing Helmholtz coils may be micromachined and disposed on opposing sides of each cantilever. Since the power requirements of a Helmholtz coil increase rapidly with size, smaller coils would provide significant savings in power consumption.

Not shown in FIG. 8 (for clarity of illustration), are a pair of permanent magnets, positioned above and below the plane of the drawing sheet, for providing the magnetizing field for the paramagnetic beads.

Alternatively, current carrying wires could be positioned above and below the cantilevers, to provide either electric field (in embodiments employing electric field) or magnetic field. As skilled practitioners will recognize, for certain embodiments of the invention, a flowing electrical current will be used to cause the electrically active species to move.

However, a nonuniform electric field (i.e., a field gradient) is needed to cause dipolar species to move. In those embodiments, means for inducing an electric field gradient will be used. However, skilled practitioners will recognized that the forces exerted on an uncharged dipolar species by a nonuniform electric field tend to be smaller than the forces exerted on an charged species by an electric field.

Arrays and Other Preferred Features

Figure 10:
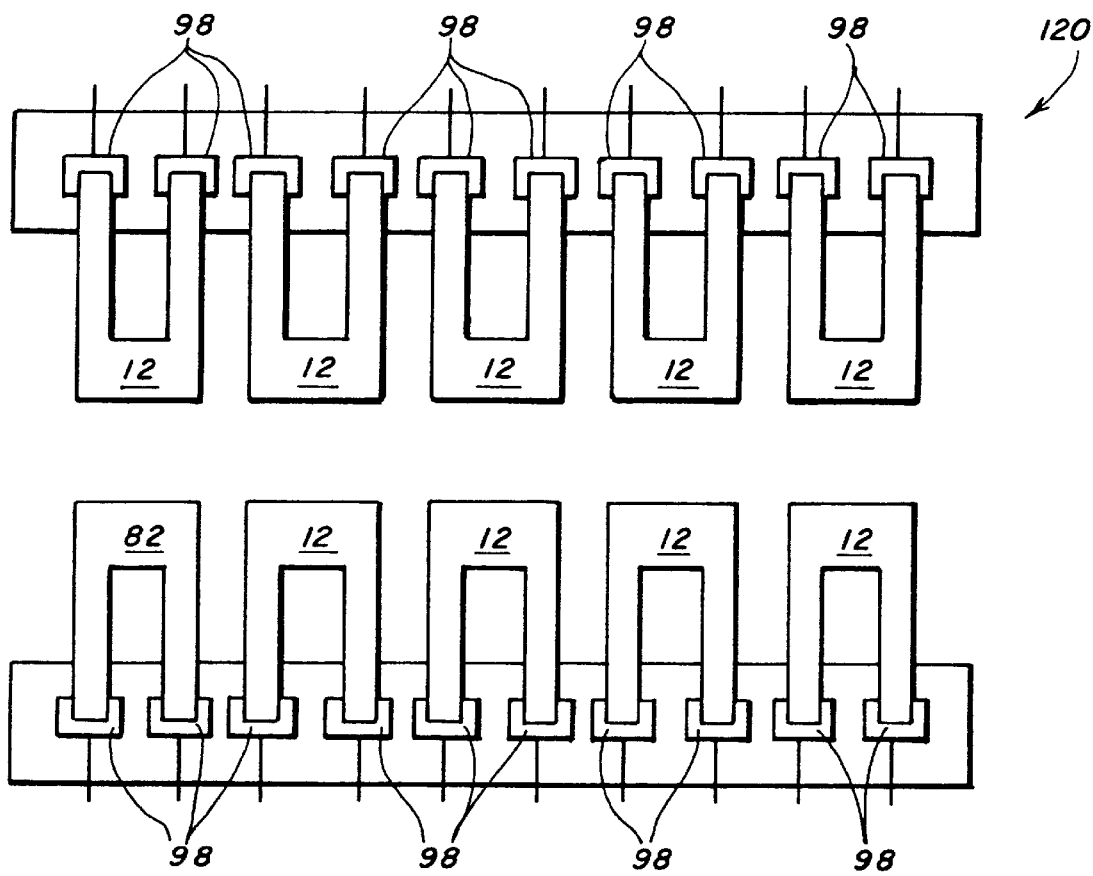
FIG. 10 shows an array of cantilevers in a preferred embodiment of the invention.

As described above, a preferred embodiment of the invention will include at least one reference cantilever for noise reduction. As shown in FIG. 10, another preferred embodiment of the invention will include an array 120 of cantilevers 12 with attached species, and preferably at least one reference cantilever 82. An array 120 according to the invention may provide several advantages, including enhanced sensitivity and dynamic range, the ability to look for several different target species simultaneously, the ability to look for several different epitopes of a target species simultaneously, and the ability to self-calibrate.

As described above, a preferred embodiment of the invention will include a time-varying electric or magnetic field, so that a signal force on the cantilever is likewise time varying. The cantilevers used in the invention will have a magnetic resonance frequency, and it will sometimes be preferred to vary the force-producing electric or magnetic field to excite that resonance, although more typically sub-resonant frequencies will be used.

In selecting the appropriate magnitude for the force acting on a structure that moves in an applied electric or magnetic field, skilled practitioners should note that this force should be large enough to cause a measurable deflection of the cantilever when this force is translated to the cantilever, but it should not be so great that the structure that moves in an applied electric or magnetic field will be separated from the cantilever, resulting in no force (or only an intermittent force) being directed to the cantilever. It should also be noted that nonselective interactions (such as hydrogen bonding) tend to be much weaker than selective interactions and thus should not be an excessive source of noise, especially when the noise reducing features of the invention are employed.

Having described the invention, the following examples are given to illustrate specific applications of the invention. These specific examples are not intended to limit the scope of the invention described in this application.

EXAMPLE 1

Identification of Biotin with Magnetic Forces in a Competitive Assay

Two AFM cantilevers were coated with biotin through the spontaneous adsorption of biotinylated bovine serum albumin (BBSA) in 0.15 mM phosphate buffer, 0.1N NaCl (PBS) at pH 5.7. A second set of control cantilevers was coated with bovine serum albumin (BSA) in PBS at pH 5.7. Streptavidin functionalized paramagnetic beads (diameter 2.5 $\mu$m, M-280 Superparamagnetic beads, streptavidin coated, Dynal Co., Lake Success, N.Y.) were placed in solution with the BSA and BBSA coated cantilevers at a concentration of 6–7$\times 10^5$ beads/ml in PBS at pH 7.0. Typical magnetic susceptibilities specified by the manufactures of commercially available paramagnetic beads vary between 8$\times 10^{-3}$ and 1.7$\times 10^{-2}$ emu/Oe cm$^3$.

Figure 11:
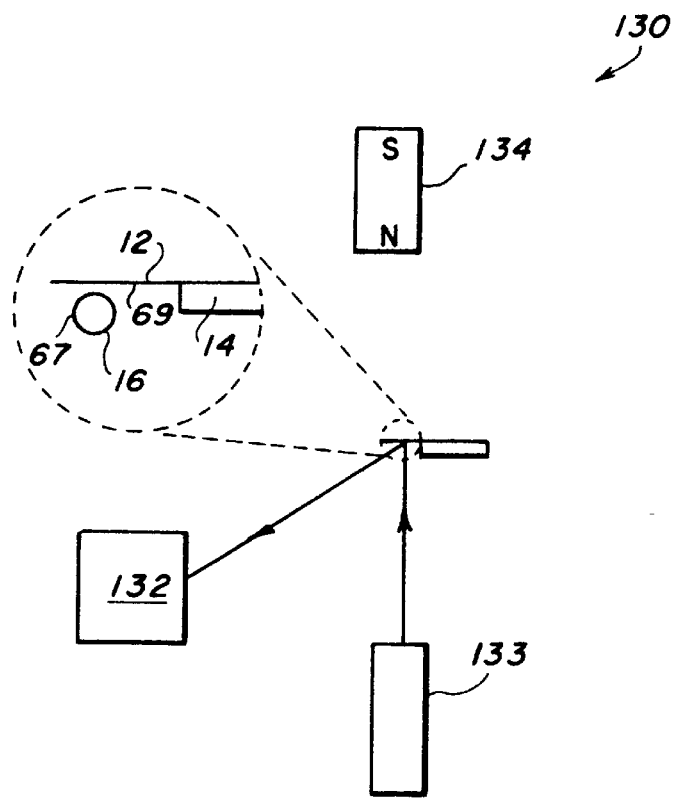
FIG. 11 shows a schematic of a sensor according to the present invention.
Figure 12:
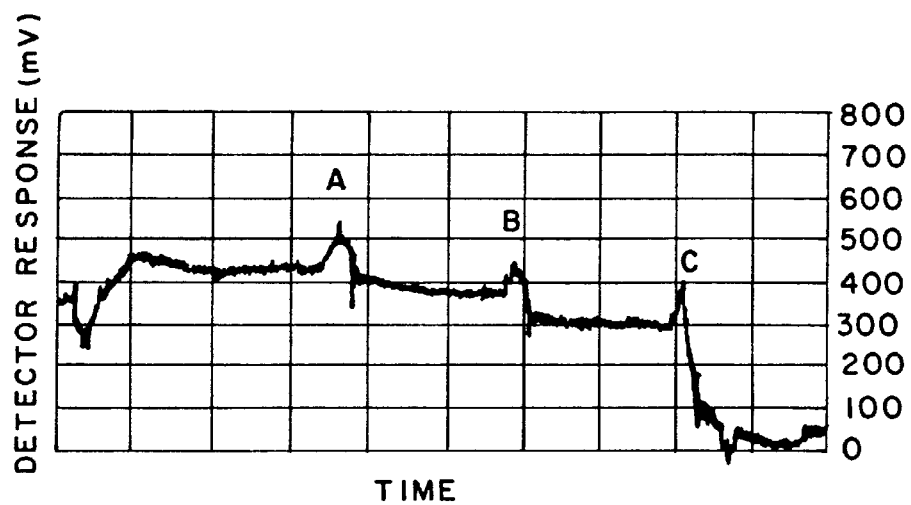
FIG. 12 shows the response of a BBSA-modified cantilever to the motion of a magnet.

FIG. 11 shows a schematic of the sensor 130 used in this experiment, including the position sensing detector 132, cantilever 12, laser 133, and magnet 134 used in the biotin detection demonstration, with a detail of the interaction of the biotin 69 coated cantilever 12 with a streptavidin 67 coated bead 16. The magnet was a 25.4$\times$10$\times$10 mm magnet with a magnetization of 1,500,000 A/m. The magnet 134 was oriented with its pole pointing in the direction of cantilever motion and moved to positions between 2 and 20 mm from the cantilever. The position of the cantilever was monitored with the optical-lever position sensitive detector. The response of the BBSA cantilever to the motion of the magnet is shown in FIG. 12. In FIG. 12, the change in the position of the cantilever is plotted in the Y-axis (mV) while the position of the magnet is related to the Y axis by the time a which the magnet was moved. The magnet was moved three times as indicated on the plot with the three points labeled A, B, and C. The spike in the response of the detector immediately after the magnet is moved results from the vibration produced by the motion of the magnet. The BBSA cantilever responds to the motion of the magnet at each of the three magnet positions.

Figure 13:
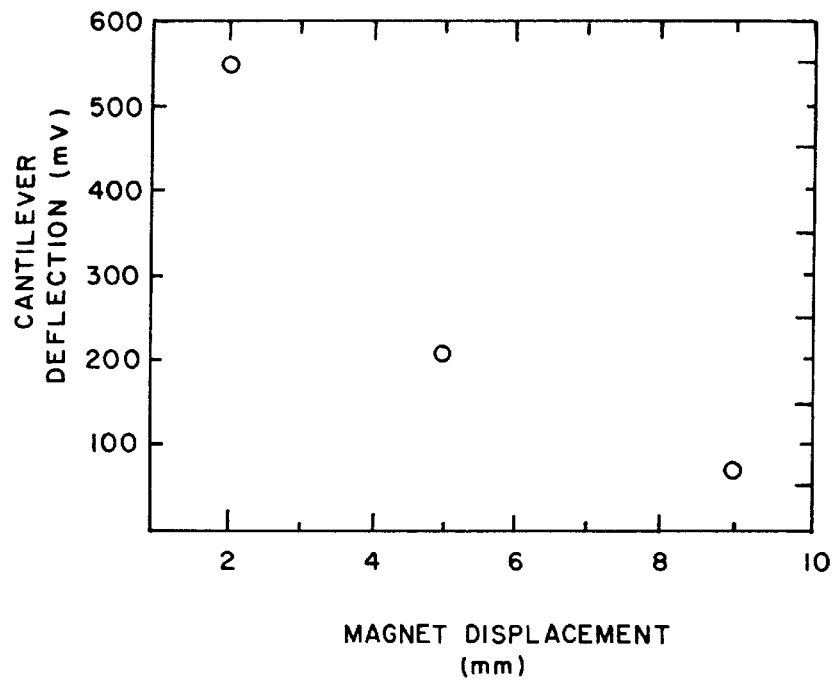
FIG. 13 shows the motion of a cantilever resulting from the displacement of a magnet as the magnet approaches the cantilever.

The motion of the cantilever resulting from the displacement of the magnet increases rapidly as the magnet approached the cantilever, as seen in FIG. 13, which is consistent predicted behavior of a paramagnetic bead and magnet. The data points represent a the average of six measurements. Note that the accuracy of the displacement of the magnet is no better than ±1 mm.

Figure 14:
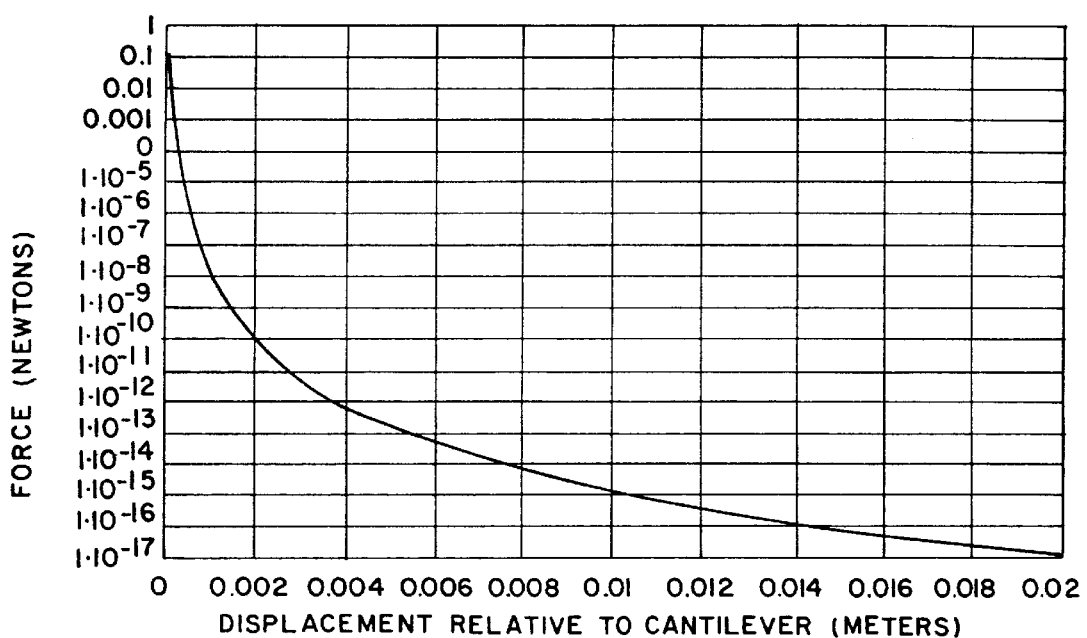
FIG. 14 shows the calculated force produced by a magnet on a paramagnetic bead.

For a single paramagnetic bead of the type used in this experiment, the force produced by a 25.4×10×10 mm magnet with a magnetization of 1,500,000 A/m may be calculated. The results are shown in FIG. 14. There were 170 superparamagnetic particles on the BBSA cantilever. The calculated forces suggest that the force applied to the cantilever by 170 superparamagnetic beads by a magnet position 2 mm from the cantilever is $\approx 3\times 10^{-8}$ N. The magnitude of individual streptavidin-biotin and DNA 20-mer interactions are 0.3 and $1.5\times 10^{-9}$ N, respectively. These results demonstrate that the paramagnetic beads can be used to apply forces in excess of single molecular recognition interactions. If the detector is constructed with a force sensitivity typical obtained for optical-lever displacement detectors ($10^{-11}$ N) the chemical detectors' sensitivity will reach a single molecular level.

Obviously, many modifications and variations of the present invention are possible in light of the above teachings. It is therefore to be understood that, within the scope of the appended claims, the invention may be practiced otherwise than as specifically described.

What is claimed is:

1. A cantilever for use in a sensor for a selected target species, wherein said cantilever has attached chemical modifiers capable of undergoing a selective binding interaction, and further comprising means for generating an electric or magnetic field in contact with said cantilever, wherein said electric or magnetic field is suitable for inducing a measurable deflection in said cantilever when said attached chemical modifiers on said cantilever are selectively bound to one or more electrically or magnetically active structures.

2. The cantilever of claim 1, wherein said attached chemical modifiers capable of undergoing a selective binding interaction are selected from the group consisting of antibodies, haptens, antigens, nucleic acids, proteins, selective binding polymers, and chelating agents.

3. The cantilever of claim 1, wherein said means for generating a field is means for generating a magnetic field.

4. The cantilever of claim 1, wherein said means for generating a field is means for generating an electric field.

5. A sensor for a selected target molecule, comprising:
a cantilever having attached chemical groups, disposed in solution and in a magnetic field; and
one or more magnetic structures, disposed in said solution, wherein said structures have been chemically modified to have a selective binding response relative to said attached chemical groups on said cantilever in the absence of said target molecule, and a different selective binding response relative to said attached chemical groups on said cantilever in the presence of said target molecule.

6. The sensor of claim 5, further comprising means for monitoring the deflection of said cantilever.

7. The sensor of claim 5, wherein said magnetic field is a time-variant magnetic field.

8. The sensor of claim 5, wherein said magnetic field is a nonuniform magnetic field and said one or more magnetic structures are one or more paramagnetic structures.

9. A method for detecting the presence of a target substance in a sample suspected of including said target substance, wherein said target substance specifically binds to species having a binding site for said target substance, comprising the steps of:
placing said sample in a solution in a nonuniform magnetic field and in contact with a cantilever modified with cantilever-bound species;
placing in said solution one or more paramagnetic structures, wherein said structures have been modified with paramagnetic structure-bound species having a selective binding response relative to said cantilever-bound species in the absence of said target substance, and a different selective binding response relative to said cantilever-bound species in the presence of said target substance; and
monitoring the deflection of said cantilever.

10. The method of claim 9, wherein said paramagnetic structure-bound species selectively bind to said target substance and said cantilever-bound species selectively bind to said target substance, whereby, in the presence of said target substance, said paramagnetic structure-bound species and said cantilever-bound species will sandwich said target substance, thereby forming a link between said paramagnetic structure and said cantilever, thereby producing a force acting on said cantilever due to the force acting on said paramagnetic structure from said magnetic field.

11. The method of claim 9, wherein said paramagnetic structures are placed in solution prior to said sample suspected of including said target substance, wherein said paramagnetic structure-bound species selectively bind to said cantilever-bound species, thereby linking said paramagnetic structure to said cantilever, and wherein said paramagnetic structure-bound species selectively bind to said target substance, thereby producing a force acting on said cantilever due to the force acting on said paramagnetic structure from said magnetic field, whereby, in the presence of said target substance, at least some of said paramagnetic structures will be displaced from said cantilever, thereby breaking said link between said paramagnetic structures and said cantilever, thereby removing said force.

12. The method of claim 9, wherein both said paramagnetic structure-bound species and said target substance selectively bind to said cantilever-bound species, whereby said paramagnetic structure-bound species and said target substance compete for binding to said cantilever-bound species.

13. A sensor for a selected target molecule, wherein said selected target molecule has, or may be modified to have, a net charge or dipole moment, comprising:
a cantilever having attached chemical groups, disposed in an electric field, wherein said attached chemical groups selectively bind to said selected target molecule; and
means for monitoring the deflection of said cantilever.

14. The sensor of claim 13, wherein said electric field is a time-variant electric field.

15. A sensor for a selected target species, comprising:
a cantilever having attached chemical groups, disposed in an electric field; and one or more charged or dipolar structures, disposed in said electric field, wherein said structures have been chemically modified to have a selective binding response relative to said attached chemical groups on said cantilever in the absence of said target species, and a different selective binding response relative to said attached chemical groups on said cantilever in the presence of said target species.

16. The sensor of claim 5, wherein said sensor does not include separation means for separating magnetic structures that bind to said cantilever from magnetic structures that do not bind to said cantilever.

17. The sensor of claim 7, wherein said time-variant magnetic field is an oscillating magnetic field.

18. The sensor of claim 17, wherein said oscillating magnetic field has an oscillating gradient $$\frac{\partial B}{\partial x}$$

19. The method of claim 9, wherein said method does not include a separation step prior to said monitoring step.

20. The sensor of claim 13, wherein said sensor does not include separation means for separating magnetic structures that bind to said cantilever from magnetic structures that do not bind to said cantilever.

21. The sensor of claim 14, wherein said time-variant electric field is an oscillating electric field.

22. The sensor of claim 21, wherein said oscillating electric field has an oscillating gradient.

23. The sensor of claim 15, wherein said sensor does not include separation means for separating magnetic structures that bind to said cantilever from magnetic structures that do not bind to said cantilever.

24. The sensor of claim 13, wherein said cantilever is disposed in gas phase.

25. The sensor of claim 13, wherein said selected target molecule has, or may be modified to have, a dipole moment, and wherein said electric field is a nonuniform electric field for applying a force to said selected target molecule.

26. The sensor of claim 15, wherein said selected charged or dipolar structures are dipolar structures, and wherein said electric field is a nonuniform electric field for applying a force to said selected dipolar structures.

27. The sensor of claim 5, wherein said magnetic field is of sufficient magnitude to separate any of said magnetic structures having a non-selective binding interaction with said cantilever from said cantilever.

28. The cantilever of claim 1, wherein said electric or magnetic field is of sufficient magnitude to separate any of said electrically or magnetically active structures having a non-selective binding interaction with said cantilever from said cantilever.

29. The method of claim 9, wherein said magnetic field is of sufficient magnitude to separate any of said magnetic structures having a non-selective binding interaction with said cantilever from said cantilever.

30. The method of claim 29, further comprising the step of the increasing the magnetic field to an intensity wherein magnetic structures having a selective binding interaction with said cantilever separate from said cantilever.

31. The sensor of claim 15, wherein said electric field is adapted for applying a force of sufficient magnitude to separate any of said charged or dipolar structures having a non-selective binding interaction with said cantilever.

32. The sensor of claim 31, wherein said electric field is adjustable to apply a force of sufficient magnitude to separate any of said charged or dipolar structures having a selective binding interaction with said cantilever.

* * * * *